US010093728B2

(12) United States Patent
Mendiratta et al.

(10) Patent No.: US 10,093,728 B2
(45) Date of Patent: Oct. 9, 2018

(54) PHARMACEUTICAL FORMULATIONS OF TNF-ALPHA ANTIBODIES

(71) Applicant: Cadila Healthcare Limited, Ahmedabad, Gujarat (IN)

(72) Inventors: Sanjeev Kumar Mendiratta, Ahmedabad (IN); Sanjay Bandyopadhyay, Ahmedabad (IN); Chintan G. Patel, Ahmedabad (IN)

(73) Assignee: CADILA HEALTHCARE LIMITED, Ahmedabad (IN)

( * ) Notice: Subject to any disclaimer, the term of this patent is extended or adjusted under 35 U.S.C. 154(b) by 145 days.

(21) Appl. No.: 14/383,533

(22) PCT Filed: Mar. 5, 2013

(86) PCT No.: PCT/IN2013/000129
§ 371 (c)(1),
(2) Date: Sep. 5, 2014

(87) PCT Pub. No.: WO2013/164837
PCT Pub. Date: Nov. 7, 2013

(65) Prior Publication Data
US 2015/0071936 A1 Mar. 12, 2015

(30) Foreign Application Priority Data

Mar. 7, 2012 (IN) .......................... 610/MUM/2012
May 30, 2012 (IN) ........................ 1606/MUM/2012
Oct. 17, 2012 (IN) ........................ 3031/MUM/2012

(51) Int. Cl.
C07K 16/24 (2006.01)
A61K 39/395 (2006.01)
A61K 9/19 (2006.01)
A61K 47/18 (2017.01)
A61K 47/26 (2006.01)

(52) U.S. Cl.
CPC .............. C07K 16/241 (2013.01); A61K 9/19 (2013.01); A61K 39/39591 (2013.01); A61K 47/183 (2013.01); A61K 47/26 (2013.01); C07K 2317/21 (2013.01); C07K 2317/76 (2013.01); C07K 2317/94 (2013.01)

(58) Field of Classification Search
None
See application file for complete search history.

(56) References Cited

U.S. PATENT DOCUMENTS 6,090,382 A    7/2000  Salfeld et al.
6,258,562 B1   7/2001  Salfeld et al.
7,592,004 B2 * 9/2009  Kaisheva ............ A61K 9/0019
                                              424/130.1
7,648,702 B2 * 1/2010  Gombotz ............. A61K 9/0019
                                              424/134.1
8,216,583 B2 * 7/2012  Kruase ................. A61K 9/19
                                              424/130.1
9,808,525 B2  11/2017  Manning et al.
2011/0305639 A1* 12/2011 Lobo ................. A61K 9/0019
                                              424/9.1

FOREIGN PATENT DOCUMENTS

WO    WO2004016286 A2    2/2004
WO    WO-2007092772 A2   8/2007
WO    WO2010077422 A2    7/2010
WO    WO-2010129469 A1  11/2010

OTHER PUBLICATIONS

Tim J Kamerzell et al: Protein excipient interactions: Mechanisms and biophysical characterization applied to protein formulation development, Advanced Drug Delivery Reviews, Elsevier, Jul. 26, 2011, pp. 1118-1159, vol. 63, No. 13.
Mark Cornell Manning et al: Stability of Protein Pharmaceuticals: An Update, Pharmaceutical Research, Kluwer Academic Publishers-Plenum Publishers, NL, Feb. 9, 2010, pp. 544-575, vol. 27. No. 4.
Robert J Falconer et al: Stabilization of a monoclonal antibody during purification and formulation by addition of basic amino acid excipients, Journal of Chemical Technology & Biotechnology, John Wiley & Sons, Inc., Jul. 7, 2011, pp. 942-948, vol. 86. No. 7.
Maity Hari Pada et al: Effects of arginine on photostability and thermal stability of IgG1 monoclonal antibodies, Current Pharmaceutical Biotechnology, Bentham Science Publishers, NL, Dec. 1, 2009, pp. 761-766, vol. 10. No. 8.
Cleland et al. (1993) "The development of stable protein formulations: a close look at protein aggregation, deamidation, and oxidation," Critical Reviews in Therapeutic Drug Carrier Systems 10(4): 307-377.
International Preliminary Report on Patentability dated Jul. 14, 2014 for International Patent Application No. PCT/IN2013/000129 (23 pages).
International Search Report dated Aug. 29, 2013 for Application No. PCT/IN2013/000129 (4 pages).
Kempeni (1999) "Preliminary results of early clinical trials with the fully human anti-TNFá monoclonal antibody D2E7," Ann Rheum Dis 58 (Suppl I): I70-I72.
Kempeni (2000) "Update on D2E7: A Fully Human Anti-Tumour Necrosis Factor ? Monoclonal Antibody," Ann Rheum Dis 59 (Supp) 1): i44-i45.
Therapeutic Peptides and Proteins: Formulation, Processing, and Delivery Systems, "Preformulation and Formulation of Therapeutic Peptides and Proteins," Chapter 4, Taylor & Francis Group, LLC, 2006, pp. 91-138.
Written Opinion dated Aug. 29, 2013, 2015 for Application No. PCT/IN2013/000129 (7 pages).
Product insert for abciximab; Eli Lilly and Company; dated Nov. 2017, 17 pages.
Product insert for abciximab; Janssen Biotech; dated Oct. 2017, 17 pages.

(Continued)

Primary Examiner — Yunsoo Kim
(74) Attorney, Agent, or Firm — Goodwin Procter LLP

(57) ABSTRACT

The present invention provides certain improved formulations of proteins. Specifically, the present invention provides use of certain excipients that are useful for stabilization of antibody preparations. Additionally, the novel formulations of the present invention prevents the formation of aggregates or fragments or modifications of protein in solution.

11 Claims, 6 Drawing Sheets

(56) References Cited

OTHER PUBLICATIONS

Product insert for alemtuzumab; Genzyme Corporation; dated Oct. 2017, 17 pages.
Product insert for basiliximab; Novartis Pharmaceutical Corporation; dated Nov. 2017, 13 pages.
Product insert for daclixumab; Abbvie; dated Aug. 2017, 39 pages.
Product insert for gemtuzumab ozogamicin; Wyeth Pharmaceuticals; dated Sep. 2017, 19 pages.
Product insert for infliximab; Janssen Biotech; dated Oct. 2017, 53 pages.
Product insert for palivizumab; Medlmmune, LLC; dated May 2017, 15 pages.
Product insert for rituximab; Genentech, Inc.; dated Apr. 2018, 43 pages.
Product insert for trastuzumab; Genentech, Inc.; dated Apr. 2017, 45 pages.
Scientific Discussion of Avastin, European Public Assessment Report Doc. # WC500029262, European Medicines Agency, 2005.
Ajay K. Banga, Therapeutic Peptides and Proteins, Formulation Processing and Delivery Systems, Chapt. 4: Preformulation and Formulation of Therapeutic Peptides and Proteins, pp. 91-148, Taylor & Francis Group, LLC, 2006.
Wang, W., Instability, stabilization, and formulation of liquid protein Pharmaceuticals, International Journal of Pharmaceutics, vol. 185, pp. 129-188, Elsevier, 1999.

* cited by examiner $A_t$ = Aggregation after exposure up to time t; $A_0$ = Aggregation before exposure (time 0)

$L_t$ = HC-Lys0 content after exposure up to time t; $L_0$ = HC-Lys0 content before exposure (time 0)

$A_t$ = Aggregation after exposure up to time t; $A_0$ = Aggregation before exposure (time 0)

$L_t$ = HC-Lys0 content after exposure up to time t; $L_0$ = HC-Lys0 content before exposure (time 0)

$A_t$ = Aggregation after exposure up to time t; $A_0$ = Aggregation before exposure (time 0)

$L_t$ = HC-Lys0 content after exposure up to time t; $L_0$ = HC-Lys0 content before exposure (time 0)

PHARMACEUTICAL FORMULATIONS OF TNF-ALPHA ANTIBODIES

CROSS-REFERENCE TO RELATED APPLICATIONS

This application claims priority to International Application No. PCT/IN2013/000129, filed on Mar. 5, 2013, which in turn claims priority to India Patent Application No. 610/MUM/2012, filed on Mar. 7, 2012, India Patent Application No. 1606/MUM/2012, filed on May 30, 2012, and Indian Patent Application No. 3031/MUM/2012, filed on Oct. 17, 2012, the contents of which are all hereby incorporated by reference.

FIELD OF THE INVENTION

The present invention relates to certain improved formulations of proteins. Specifically, the present invention provides use of certain excipients that are useful for stabilization of antibody preparations. Additionally, the novel formulation of the present invention prevents the formation of aggregates or fragments or modification of protein in solution during storage.

BACKGROUND OF THE INVENTION

Proteins are large and complex molecules. They are required to be in their native confirmation in order to remain biologically active and not be immunogenic. Proteins having a high pI value or distinct polarity may not show stability in solution at or around physiological pH conditions. Further, at high concentration, protein molecules in solution are susceptible to undergo aggregation or degradation or certain modifications with time during storage. Most common protein degradation pathways known from literature are protein aggregation, deamidation and oxidation [Cleland et al. Critical Reviews in Therapeutic Drug Carrier Systems 10(4): 307-377 (1993)]. Degradation of protein during storage may take place due to chemical instability (i.e. any process which involves modification of the protein by bond formation or cleavage resulting in a new chemical entity) or physical instability (i.e. changes in the higher order structure of the protein). Chemical instability majorly can be result of deamidation, racemization, hydrolysis, oxidation, beta elimination or disulfide exchange. Physical instability can result from denaturation, aggregation, precipitation or adsorption. In an aspect, the present invention discloses suitable formulation of antibody proteins. Antibodies are highly complex molecules and are the fastest growing class of biologics in the pharmaceutical industry due to their therapeutic effectiveness in humans. However, antibodies are subject to undergo aggregation or degradation or denaturation or chemical modifications resulting in the loss of biological activity during the manufacturing process and/or during storage with time. Such protein modifications can also make them immunogenic resulting in the generation of anti-drug antibodies by the patient which can reduce the drug availability during subsequent injections or worse induce an autoimmune reaction. Therefore, there is a need to have stable new formulations for antibody preparations which protect the molecules from aggregation or degradation or chemical modification during the manufacturing process and/or storage in liquid solution even at high protein concentration while preserving the active biological conformation of the antibody molecules.

Liquid pharmaceutical formulation is a primary choice for manufacturers to prepare a stable, safe and effective pharmaceutical preparation of antibody for therapy. Liquid pharmaceutical preparation is also considered to be easy-to-handle for the patients and by the patients. However, a long appreciated problem with liquid formulations of protein therapeutics is that of aggregation, where protein molecules physically stick together, for example, resulting in the formation of either soluble high molecular weight protein aggregates or insoluble protein aggregates, which may cause undesired immunological reactions in patients upon administration. Additionally, a major problem caused by the aggregate formation is that during the administration the formulation may block syringes or pumps rendering it unsafe to patients. Aggregation of protein can also significantly impact its potency, immunogenicity and stability. Another reason of degradation is that unfolding mediated adsorption at interfaces can often be an initiating step for irreversible aggregation in solution. In this respect, proteins tend to adsorb at liquid-solid, liquid-air, and liquid-liquid interfaces. Sufficient exposure of a protein's core at a hydrophobic surface can result in adsorption as a consequence of agitation, temperature or pH induced stresses. Further, proteins also are sensitive to, for example, pH, ionic strength, thermal stress, shear and interfacial stresses, all of which can lead to aggregation and result in instability. Another consequence of aggregation is particle formation, an important consideration in liquid and lyophilized protein pharmaceuticals.

WO 2004/016286 discloses a liquid formulation for stabilizing antibodies which treat TNF α mediated diseases, comprising the antibody, a buffer system, mannitol, polysorbates and tonicity agents. The formulation uses a citrate-phosphate buffer system. This formulation could be thawed/frozen at least 3 times without any detrimental effect on either the chemical and physicochemical properties or biological activity.

In order to realize the clinical potency of an antibody protein, there is a need for new and improved formulations comprising the antibody molecule(s) in its native conformation, which can be stored under a desired/suitable condition for long-term storage without formation of significant amount of aggregates or fragments or modified variants of the antibody protein, even at high protein concentration. The present invention addresses the above-identified need by providing novel stable formulations comprising an antibody molecule, preferably a monoclonal antibody, along with suitable excipients which makes the formulation stable and having sufficiently low viscosity at around physiological osmolality and which is therefore suitable for administration to mammals, particularly human subjects.

We herein disclose some such formulations which prevent the formation of aggregates during and after formulation while providing a suitable condition for long term storage.

EMBODIMENTS OF THE INVENTION

The invention provides improved liquid formulation comprising therapeutic amount of proteins preferably antibodies and suitable excipients.

In certain embodiments the present invention provides a liquid formulation suitable for human use which comprises a therapeutic amount of monoclonal antibody or antigen binding portion thereof, which binds to tumor necrosis factor (TNF) aid suitable excipients optionally selected from suitable buffers, stabilizer(s), surfactant(s) and suitable additives for maintaining osmolality, optionally with other excipients.

In an embodiment the present invention provides a liquid formulation which comprises of monoclonal antibodies or antigen binding portion thereof along with suitable buffer(s) and other excipients optionally selected from one or more stabilizers, surfactants and tonicity agents such as sodium chloride or potassium chloride. In an embodiment, such formulations can also optionally be lyophilized. Lyophilization can be performed by a skilled person using the techniques available in the art which includes various steps like freezing, annealing, primary drying and secondary drying.

In yet another embodiment the present invention provides a liquid formulation also suitable for lyophilization which comprises from about 1 mg/mL to about 160 mg/mL of monoclonal antibody or antigen binding portion thereof and suitable buffers at a concentration of about 5 mM to 100 mM, optionally suitable stabilizers with a concentration of about 1% to 10%, optionally suitable surfactants at a concentration of about 0.001% to 1% and optionally suitable tonicity agents at a concentration of about 10 mM to about 150 mM.

In an embodiment, the present invention provides a liquid formulation buffered between pH 4 to 8.

In another embodiment, the present invention provides a liquid formulation which can be used for parenteral administration. Parenteral administration includes intravenous, subcutaneous, intra peritoneal, intramuscular administration or any other route of delivery generally considered to be falling under the scope of parenteral administration and as is well known to a skilled person.

In another embodiment, the present invention provides a liquid formulation which improves stability and prevents formation of aggregates of protein in the said formulation. Generally, a stable formulation is the one which retains its physical stability and/or chemical stability and/or biological activity over a period of time upon storage.

In a further embodiment, the present invention provides a liquid formulation which can be used for administering to a patient suffering from a disorder in which TNFα activity is detrimental. Such disorders include sepsis, infections, autoimmune diseases, transplant rejection, malignancy, pulmonary disorders, cardiac disorders, intestinal disorders, graft-versus-host disease and the like. Such disorders occur due to TNFα activity and are well described in literature such as in U.S. Pat. No. 6,09,382.

BRIEF DESCRIPTION OF THE ACCOMPANYING DRAWINGS

DETAILED DESCRIPTION OF THE INVENTION

Figure 1:
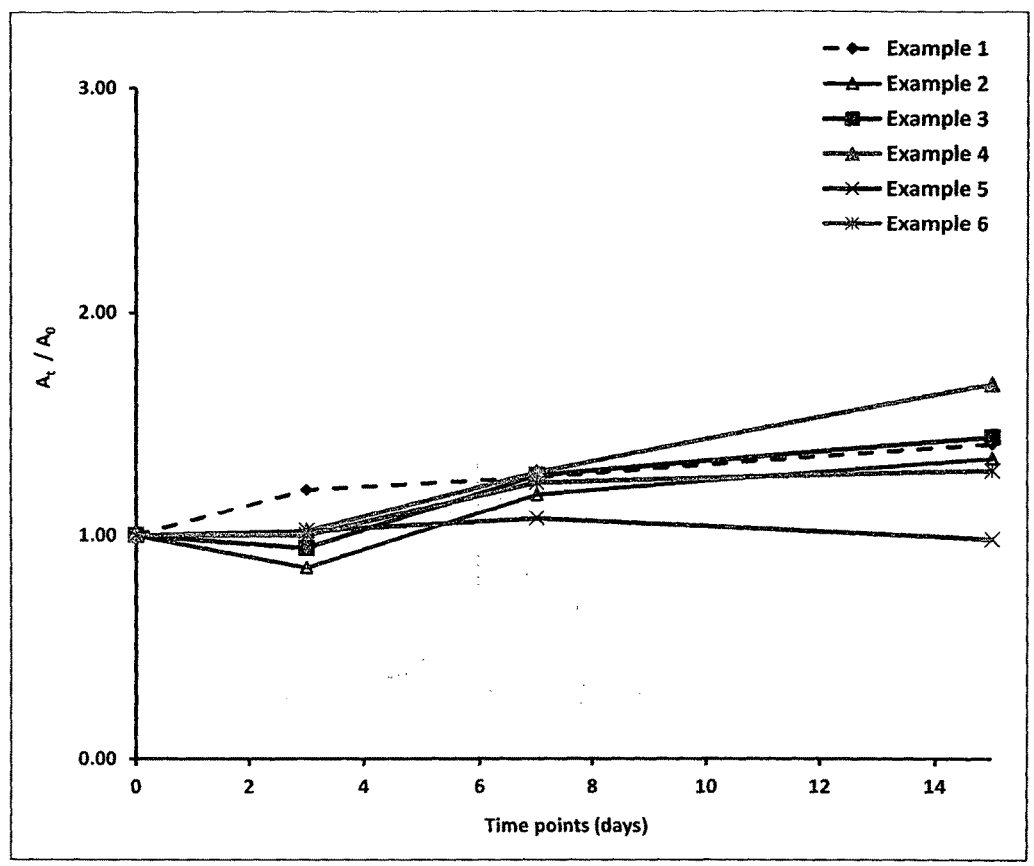
FIG. 1 shows the level of aggregates of Adalimumab protein formulated in citrate-phosphate buffer with different stabilizer(s), bulking agent and an isotonicity agent during storage under stressed condition. Formulation compositions are described with Examples 1 to 6.

The present invention provides novel and improved liquid formulations which can optionally be lyophilized, comprising of suitable amount of therapeutic protein(s), preferably monoclonal antibodies, in suitable buffer(s), one or more suitable stabilizers, and other excipients which are optionally selected from suitable surfactants and tonicity agents. The said formulation prevents formation of aggregates of protein (antibody) and maintains the potency and stability of the therapeutic compound for up to the desired period of time.

In such embodiment the protein is an antibody or antigen binding portion thereof. In a preferred embodiment the antibody is selected from suitable polyclonal, monoclonal, recombinant antibodies, single chain antibodies, hybrid antibodies, chimeric antibodies, humanized antibodies, or fragments thereof, isolated human antibodies or antibody portions thereof or antibody-like molecules containing one or two binding sites for an antigen and an Fc-part of an immunoglobulin. Adalimumab and Infliximab are examples of antibodies or more suitably, monoclonal antibodies. Infliximab is example of chimeric antibody. Adalimumab is example of human antibody. Etanercept is an example of antibody like molecules. In a preferred embodiment, antibodies used in the formulation are human antibodies. In a more preferred embodiment, the antibodies used in the formulation are human antibodies directed to TNFα including human TNFα. In a still further embodiment, the formulation includes D2E7 and combination of D2E7 with other antibodies. D2E7 antibody which is known by the generic name Adalimumab, with its high affinity binding to hTNFα with low dissociation kinetics and high neutralizing capacity is described in U.S. Pat. No. 6,090,382 and U.S. Pat. No. 6,258,562, as well as several publications such as *Ann Rheum Dis* 1999; 58:(Suppl I) 170-172, *Ann Rheum Dis* 2000; 59(suppl. I):i44-i45 etc. all of which are incorporated herein in their entirety. Adalimumab is available in the market with the brand name HUMIRA®. The names Adalimumab and D2E7 whenever used in the specification represent the same human monoclonal antibody as described in the above references.

In a preferred embodiment, the monoclonal antibody is Adalimumab or antigen binding portion, thereof.

In some embodiments the monoclonal antibodies or antigen binding portion thereof is generally present in a therapeutic amount of up to 160 mg/mL. In a preferred embodiment the therapeutic amount is about 1 mg/mL to about 100 mg/mL. In a more preferred embodiment the therapeutic amount is about 1 mg/mL to about 50 mg/mL.

The liquid formulation comprises a suitable buffer along with other pharmaceutically acceptable excipients, which stabilizes the pharmaceutical preparation. Suitable buffers which can be used are selected from those which are known in the art and can be found in the literature. In an embodiment the suitable buffers comprise but are not limited to histidine-buffers, citrate-buffers, succinate-buffers, acetate-buffers, phosphate-buffers, phosphate buffered saline, citrate and phosphate buffer, tromethamine buffers and the like or their suitable mixtures.

In a preferred embodiment the suitable buffer comprises of a succinate-buffer or acetate-buffer or histidine buffer. In a still preferred embodiment the suitable buffer comprises a succinate-buffer or an acetate-buffer. In a further preferred embodiment the suitable buffer comprises a succinate-buffer. Succinate buffer can be prepared by dissolving sodium succinate in sterile water or Water for Injection (WFI) or by titrating succinic acid with sodium hydroxide.

The buffers are generally used in concentrations of about 1 mM to about 100 mM. In a preferred embodiment the buffer concentration is about 5 mM to about 50 mM. In a more preferred embodiment the buffer concentration is about 10 mM to about 20 mM. In a still more preferred embodiment the buffer concentration is about 10 mM.

In an embodiment the liquid formulation maintains a pH value ranging from 4.0 to about 8.0 depending on the monoclonal antibody being used. In a preferred embodiment the buffer used maintains the pH of the formulation in the range of about 5.0 to 5.5. In a more preferred embodiment the pH is maintained to about 5.2.

The liquid formulation further comprises suitable surfactants which are pharmaceutically acceptable excipients used to protect the protein formulations against various stress conditions, like agitation, shearing, exposure to high temperature etc. The suitable surfactants include but are not limited to polyoxyethylensorbitan fatty acid esters (Tween), polyoxyethylene alkyl ethers (e.g. Brij), alkylphenylpolyoxyethylene ethers (e.g. Triton-X), polyoxyethylene-polyoxypropylene copolymer (e.g. Poloxamer, Pluronic), sodium dodecyl sulphate (SDS) and the like. In a preferred embodiment the suitable surfactant is polyoxyethylenesorbitan-fatty acid esters (Tweens). In a more preferred embodiment the polyoxyethylenesorbitan-fatty acid esters are polysorbate 20, (sold under the trademark Tween 20™) and polysorbate 80 (sold under the trademark Tween 80™). In another preferred embodiment the suitable surfactant is polyethylene-polypropylene copolymers which are sold under the names Pluronic (R). F68 or Poloxamer 188™. In another preferred embodiment the suitable surfactant is alkylphenolpolyoxyethylene esters which are sold under the trade name Triton-X.

In a preferred embodiment the surfactant is Polysorbate 80 or Polysorbate 20. In a more preferred embodiment the surfactant is Polysorbate 80.

The surfactants are generally used in concentrations of about 0.001% to about 1%. In a preferred embodiment surfactant concentration is about 0.01% to about 1%.

The liquid formulation further comprises one or more suitable stabilizer(s) which are pharmaceutically acceptable excipients, which protect the active pharmaceutical ingredient from chemical and/or physical degradation during manufacturing, storage and application. In an embodiment the stabilizers include but are not limited to suitable sugars, amino acids, polyols, cyclodextrines and the like or suitable derivative or mixtures thereof.

In one such embodiment the sugar is a monosaccharide or an oligosaccharide. Monosaccharide sugars include but are not limited to glucose, fructose, galactose, mannose, sorbose, ribose, deoxyribose and the like or amino sugars, like neuraminic acid. An oligosaccharide includes but is not limited to sucrose, trehalose, lactose, maltose and raffinose and the like or suitable mixtures, thereof.

In another embodiment the polyols which can be used as stabilizers include but are not limited to mannitol, sorbitol, dextran, glycerol, arabitol, propylene glycol, polyethylene glycol and the like or suitable combinations thereof. In a preferred embodiment the suitable polyol is sorbitol.

In another preferred embodiment the stabilizer is a polyol preferably sorbitol. In an embodiment the sorbitol is present in amount about 1% to about 10%.

In another such embodiment the amino acids which can be used as stabilizers include but are not limited to arginine, glycine, lysine, histidine, glutamic acid, aspartic acid, isoleucine, leucine, alanine, phenylalanine, tyrosine, tryptophane, methionine, serine, proline, cysteine/cystine and the like or suitable combination of any the above. In a preferred embodiment the suitable amino acid is arginine or lysine.

In an embodiment the amino acid is present in amount about 0.5% to about 10%.

In another embodiment cyclodextrines or derivative thereof, which can be used as stabilizers, includes but are not limited to α-cyclodextrin, β-cyclodextrin, γ-cyclodextrin, or their hydroxypropylated, hydroxyethylated, ethylated or methylated derivatives thereof or Sulfobutyl ether beta-cyclodextrin (SBE-beta-CD) or a branched cyclodextrins or cyclodextrin polymers or suitable mixture thereof. In a preferred embodiment the suitable cyclodextrin variant is hydroxypropylated cyclo beta-dextrin (HP-β-CD).

In a preferred embodiment the cyclodextrin or derivative is present in amount about 0.2% to about 10%.

In another embodiment the liquid formulation optionally comprises tonicity agents such as sodium chloride or potassium chloride. In a preferred embodiment, the tonicity agent is sodium chloride which is present in amount about 10 mM to about 150 mM.

The formulation may additionally further comprise one or suitable other excipients which are well known to a person skilled in the art.

In some embodiments, the liquid formulation maintains the storage stability in terms of not allowing any further protein aggregation or modifications as compared to time point zero of stability.

In some embodiments, the liquid formulation maintains the stability during the process of formulation.

To estimate the level of aggregates and the principal charged variant of Adalimumab protein, analytical HP-size exclusion chromatography and HP-ion exchange chromatography were performed, respectively.

The said analytical methods used in the present invention are well known to a skilled person and a brief description of the same is provided below merely for the sake of reference only.

HP-Size Exclusion Chromatography (HP-SEC):

Samples were analyzed to estimate the aggregates by HP-size exclusion chromatography (HP-SEC) using TSK gel G3000 SWXL column (7.8 mm I.D×30 cm L). Samples were loaded and eluted isocratically using sodium phosphate buffer at a flow rate of 0.5 mL/min. Elution was monitored at UV 214 nm.

HP-Ion Exchange Chromatography (HP-IEC):

Samples were analyzed to estimate the principal charged variant by HP-IEC using analytical cation exchange column. Samples were loaded and eluted using salt gradient at a flow rate of 1.0 mL/min. Elution was monitored at UV 280 nm.

The present invention is illustrated further in the following examples which are provided for illustration purpose and should not be construed as being a limitation to the scope of the invention.

EXAMPLES

The following non-limiting examples describe the different formulations which can be prepared as per the present invention. It will be appreciated that other excipients may be added as are necessary to these formulations and such addition of excipients are within the scope of a person skilled in the art and are to be included within the scope of the present invention.

Screening of excipients is carried out by formulating the Adalimumab protein in different compositions with different excipients and exposing them to higher temperature over the period of time. Formulations of Adalimumab protein were prepared in the presence of different buffering agent(s), stabilizer(s), bulking agent(s) and isotonicity agent(s) as exemplified below.

Example 1

| Formulation composition | |
|---|---|
| Active Ingredient | |
| Adalimumab | 50 mg/mL |
| Inactive Ingredients | |
| Dibasic sodium phosphate dihydrate | 1.53 mg/mL |
| Monobasic sodium phosphate dihydrate | 0.86 mg/mL |
| Sodium citrate | 0.3 mg/mL |
| Citric acid | 1.3 mg/mL |
| Mannitol | 12 mg/mL |
| Sodium Chloride | 6.16 mg/mL |
| Polysorbate 80 | 1 mg/mL |

Figure 2:
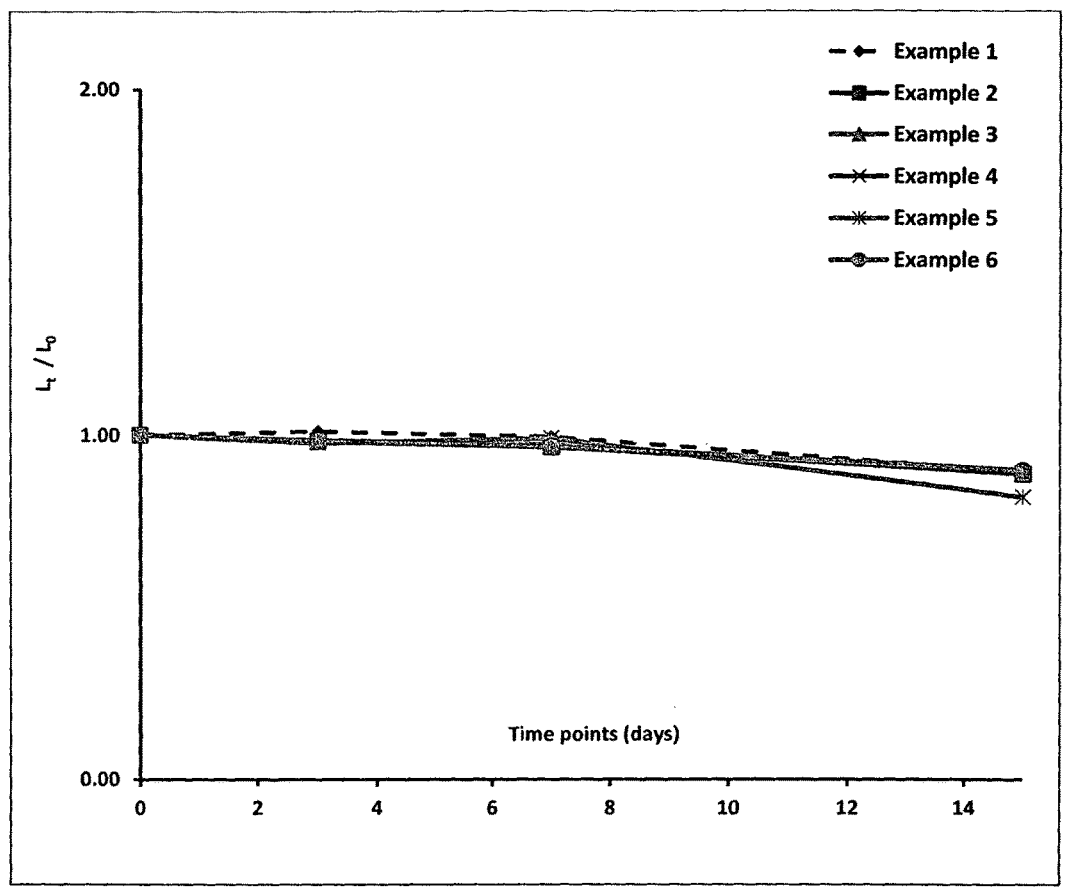
FIG. 2 shows the level of principal charged variant of Adalimumab protein formulated in citrate-phosphate buffer with different stabilizer(s), bulking agent and an isotonicity agent during storage under storage condition. Formulation compositions are described with Examples 1 to 6.

Adalimumab protein was purified as per the technique known in the art. In this example, the purified Adalimumab protein was formulated in the presence of citrate-phosphate buffer along with a stabilizer, a bulking agent and an isotonicity agent at a desired concentration as described above. pH of the formulation medium was adjusted to around pH 5.2. Excipients were added to the protein solution from respective stock solutions to adjust the final concentration and the volume was made up to the desired level with sterile water or Water for Injection. The formulated bulk was distributed in suitable container-closure systems (like vials, syringes etc.) for storage. Samples at different time points were taken out and analyzed to estimate the aggregates and the principal charged variant of Adalimumab protein by HP-Size exclusion chromatography and HP-IEC, respectively. Results are shown in FIGS. 1 and 2.

Example 2

| Formulation composition | |
|---|---|
| Active Ingredient | |
| Adalimumab | 50 mg/mL |
| Inactive Ingredients | |
| Dibasic sodium phosphate dihydrate | 1.53 mg/mL |
| Monobasic sodium phosphate dihydrate | 0.86 mg/mL |
| Sodium citrate | 0.3 mg/mL |
| Citric acid | 1.3 mg/mL |
| Mannitol | 12 mg/mL |
| Arginine | 5 mg/mL |
| Sodium Chloride | 6.16 mg/mL |
| Polysorbate 80 | 1 mg/mL |

Adalimumab protein was prepared as per the technique known in the art and formulated in the same formulation medium as described with Example 1 in the presence of Arginine. pH of the formulation medium was adjusted to around pH 5.2. Excipients were added to the protein solution from respective stock solutions to adjust the final concentration and volume was made up to the desired level with Water for Injection. The formulated bulk was distributed in suitable container-closure systems (like vials, syringes etc.) for storage. Samples were exposed to the higher temperature for checking the degradation over a period of time. Samples at different time points were taken out and analyzed to estimate the aggregates and the principal charged variant of Adalimumab protein by HP-Size exclusion chromatography and HP-IEC, respectively. Results are shown in FIGS. 1 and 2.

Example 3

| Formulation composition | |
|---|---|
| Active Ingredient | |
| Adalimumab | 50 mg/mL |
| Inactive Ingredients | |
| Dibasic sodium phosphate dihydrate | 1.53 mg/mL |
| Monobasic sodium phosphate dihydrate | 0.86 mg/mL |
| Sodium citrate | 0.3 mg/mL |
| Citric acid | 1.3 mg/mL |
| Mannitol | 12 mg/mL |
| Arginine | 5 mg/mL |
| Sorbitol | 10 mg/mL |
| Sodium Chloride | 6.16 mg/mL |
| Polysorbate 80 | 1 mg/mL |

Adalimumab protein was prepared as per the technique known in the art and formulated in the same formulation medium as described in Example 1 with the addition of arginine and sorbitol. pH of the formulation medium is adjusted to around pH 5.2. Excipients were added to the protein solution from respective stock solutions to adjust the final concentration and volume was made up to the desired level with sterile water or Water for Injection. The formulated bulk was distributed in suitable container-closure systems (like vials, syringes etc.) for storage. Samples were exposed to the higher temperature for checking the degradation over a period of time. Samples at different time points were taken out and analyzed to estimate the aggregates and the principal charged variant of Adalimumab protein by HP-Size exclusion chromatography and HP-IEC, respectively. Results are shown in FIGS. 1 and 2.

Example 4

| Formulation composition | |
|---|---|
| Active Ingredient | |
| Adalimumab | 50 mg/mL |
| Inactive Ingredients | |
| Dibasic sodium phosphate dihydrate | 1.53 mg/mL |
| Monobasic sodium phosphate dihydrate | 0.86 mg/mL |
| Sodium citrate | 0.3 mg/mL |
| Citric acid | 1.3 mg/mL |
| Mannitol | 12 mg/mL |
| Hydroxypropyl beta cyclodextrin | 20 mg/mL |
| Sodium Chloride | 6.16 mg/mL |
| Polysorbate 80 | 1 mg/mL |

Adalimumab protein was prepared as per the technique known in the art and formulated in the same formulation medium as described in Example 1 with the addition of hydroxypropyl beta cyclodextrin. pH of the formulation medium was adjusted to around pH 5.2. Excipients were added to the protein solution from respective stock solutions to adjust the final concentration and volume was made up to the desired level with sterile water or Water for Injection. The formulated bulk was distributed in suitable container-closure systems (like vials, syringes etc.) for storage. Samples were exposed to the higher temperature for checking the degradation over a period of time. Samples at different time points were taken out and analyzed mainly for presence of aggregates and HC-Lys0 content by HP-Size exclusion chromatography and HP-IEC respectively. Obtained results are shown in FIGS. 1 and 2.

Example 5

| Formulation composition | |
|---|---|
| Active Ingredient | |
| Adalimumab | 50 mg/mL |
| Inactive Ingredients | |
| Dibasic sodium phosphate dihydrate | 1.53 mg/mL |
| Monobasic sodium phosphate dihydrate | 0.86 mg/mL |
| Sodium citrate | 0.3 mg/mL |
| Citric acid | 1.3 mg/mL |
| Mannitol | 12 mg/mL |
| Hydroxypropyl beta cyclodextrin | 20 mg/mL |
| Sorbitol | 10 mg/mL |
| Sodium Chloride | 6.16 mg/mL |
| Polysorbate 80 | 1 mg/mL |

Adalimumab protein was prepared as per the technique known in the art and formulated in the same formulation medium as described with Example 1 in the presence of hydroxypropyl beta cyclodextrin and sorbitol. pH of the formulation medium was adjusted to around pH 5.2. Excipients were added to the protein solution from respective stock solutions to adjust the final concentration and volume was made up to the desired level with sterile water or Water for Injection. The formulated bulk was distributed in suitable container-closure systems (like vials, syringes etc.) for storage. Samples were exposed to the higher temperature for checking the degradation over a period of time. Samples at different time points were taken out and analyzed to estimate the aggregates and the principal charged variant of Adalimumab protein by HP-Size exclusion chromatography and HP-IEC, respectively. Results are shown in FIGS. 1 and 2.

Example 6

| Formulation composition | |
|---|---|
| Active Ingredient | |
| Adalimumab | 50 mg/mL |
| Inactive Ingredients | |
| Dibasic sodium phosphate dihydrate | 1.53 mg/mL |
| Monobasic sodium phosphate dihydrate | 0.86 mg/mL |
| Sodium citrate | 0.3 mg/mL |
| Citric acid | 1.3 mg/mL |
| Mannitol | 12 mg/mL |
| Lysine | 5 mg/mL |
| Sodium Chloride | 6.16 mg/mL |
| Polysorbate 80 | 1 mg/mL |

Adalimumab protein was prepared as per the technique known in the art and formulated in the same formulation medium as described in Example 1 with the addition of lysine. pH of the formulation medium was adjusted to around pH 5.2. Excipients were added to the protein solution from respective stock solutions to adjust the final concentration and volume was made up to the desired level with sterile water or Water for Injection. The formulated bulk was distributed in suitable container-closure systems (like vials, syringes etc.) for storage. Samples were exposed to the higher temperature for checking the degradation over a period of time. Samples at different time points were taken out and analyzed to estimate the aggregates and the principal charged variant of Adalimumab protein by HP-Size exclusion chromatography and HP-IEC, respectively. Results are shown in FIGS. 1 and 2.

Example 7

| Formulation composition | |
|---|---|
| Active Ingredient | |
| Adalimumab | 50 mg/mL |
| Inactive Ingredients | |
| Sodium succinate | 20 mM |
| Sodium chloride | 110 mM |
| Sorbitol | 50 mg/mL |
| Arginine | 10 mg/mL |
| Polysorbate 80 | 0.1 mg/mL |

Figure 3:
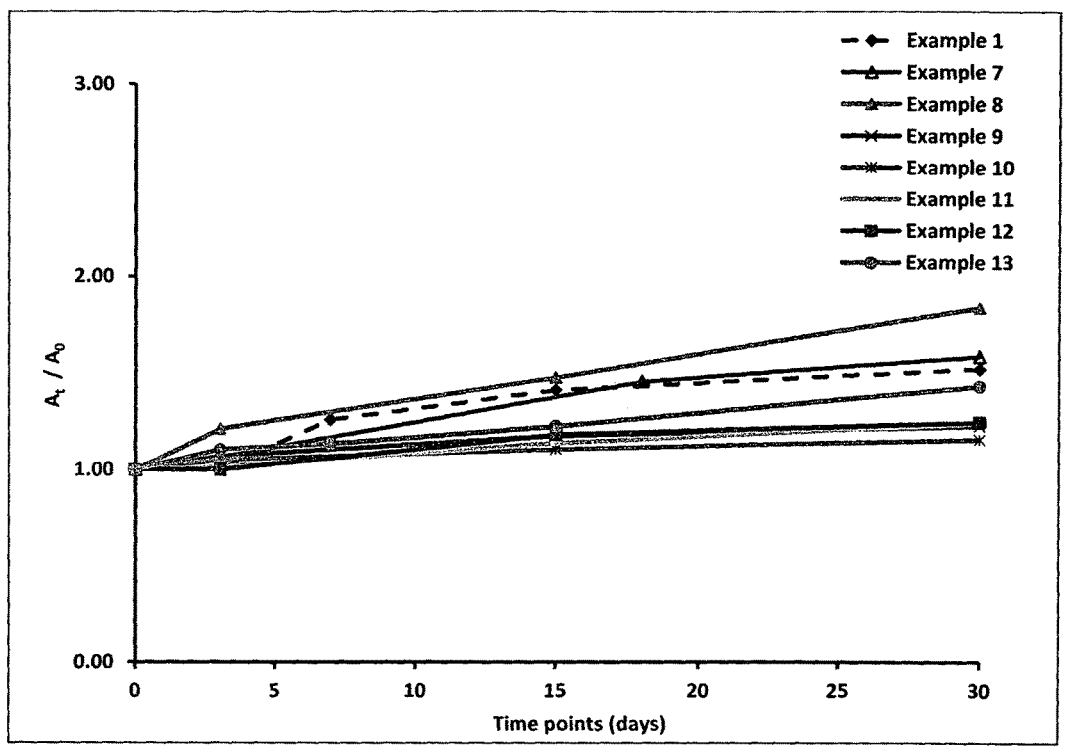
FIG. 3 shows the level of aggregates of Adalimumab protein formulated in sodium succinate buffer with different stabilizer(s), bulking agent and an isotonicity agent during storage under stressed condition. Formulation compositions are described with Examples 7 to 13.
Figure 4:
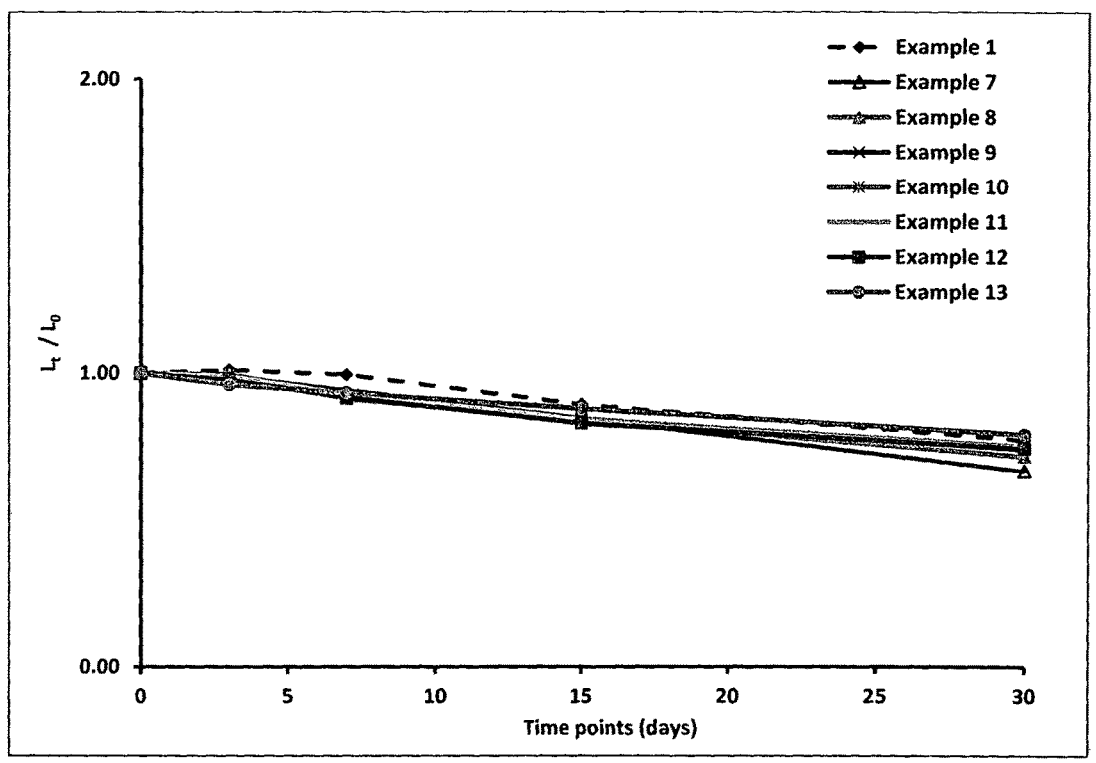
FIG. 4 shows the level of principal charged variant of Adalimumab protein formulated in sodium succinate buffer with different stabilizer(s), bulking agent and an isotonicity agent during storage under stressed condition. Formulation compositions are described with Examples 7 to 13.

Adalimumab protein was prepared as per the technique known in the art and formulated in the presence of succinate buffer containing arginine and sorbitol as stabilizers, a bulking agent and an isotonicity agent at a desired concentration as described above in formulation composition. pH of the formulation medium was adjusted to around pH 5.2. Excipients were added to the protein solution from respective stock solutions to adjust the final concentration and volume was made up to the desired level with sterile water or Water for Injection. The formulated bulk was distributed in suitable container-closure systems (like vials, syringes etc.) for storage. Samples were exposed to the higher temperature for checking the degradation over a period of time. Samples at different time points were taken out and analyzed to estimate the aggregates and the principal charged variant of Adalimumab protein by HP-Size exclusion chromatography and HP-IEC, respectively. Results are shown in FIGS. 3 and 4.

Example 8

| Formulation composition | |
|---|---|
| Active Ingredient | |
| Adalimumab | 50 mg/mL |
| Inactive Ingredients | |
| Sodium succinate | 20 mM |
| Sodium chloride | 110 mM |
| Polysorbate 80 | 0.1 mg/mL |

Adalimumab protein was prepared as per the technique known in the art and formulated in the absence of stabilizers. The formulation medium comprises a succinate buffer, a bulking agent and an isotonicity agent at a desired concentration as described above. pH of the formulation medium was adjusted to around pH 5.2. Excipients were added to the protein solution from respective stock solutions to adjust the final concentration and volume was made up to the desired level with sterile water or Water for Injection. The formulated bulk was distributed in suitable container-closure systems (like vials, syringes etc.) for storage. Samples were exposed to the higher temperature for checking the degradation over a period of time. Samples at different time points were taken out and analyzed to estimate the aggregates and the principal charged variant of Adalimumab protein by HP-Size exclusion chromatography and HP-IEC, respectively. Results are shown in FIGS. 3 and 4.

Example 9

| Formulation composition | |
|---|---|
| Active Ingredient | |
| Adalimumab | 50 mg/mL |
| Inactive Ingredients | |
| Sodium succinate | 20 mM |
| Sodium chloride | 110 mM |
| Arginine | 10 mg/mL |
| Polysorbate 80 | 0.1 mg/mL |

Adalimumab protein was prepared as per the technique known in the art and formulated in the presence of succinate buffer further comprising arginine as a stabilizer, a bulking agent and an isotonicity agent at a desired concentration as described above. pH of the formulation medium was adjusted to around pH 5.2. Excipients were added to the protein solution from respective stock solutions to adjust the final concentration and volume was made up to the desired level with sterile water or Water for Injection. The formulated bulk was distributed in suitable container-closure systems (like vials, syringes etc.) for storage. Samples at different time points were taken out and analyzed to estimate the aggregates and the principal charged variant of Adalimumab protein by HP-Size exclusion chromatography and HP-IEC, respectively. Results are shown in FIGS. 3 and 4.

Example 10

| Formulation composition | |
|---|---|
| Active Ingredient | |
| Adalimumab | 50 mg/mL |
| Inactive Ingredients | |
| Sodium succinate | 20 mM |
| Sodium chloride | 110 mM |
| Trehalose | 50 mg/mL |
| Arginine | 10 mg/mL |
| Polysorbate 80 | 0.1 mg/mL |

Adalimumab protein was prepared as per the technique known in the art and formulated in the presence of succinate buffer along with arginine and trehalose as stabilizers, a bulking agent and an isotonicity agent at a desired concentration as described above in the formulation composition. pH of the formulation medium was adjusted to around pH 5.2. Excipients were added to the protein solution from respective stock solutions to adjust the final concentration and volume was made up to the desired level with sterile water or Water for Injection. The formulated bulk was distributed in suitable container-closure systems (like vials, syringes etc.) for storage. Samples were exposed to the higher temperature for checking the degradation over a period of time. Samples at different time points were taken out and analyzed to estimate the aggregates and the principal charged variant of Adalimumab protein by HP-Size exclusion chromatography and HP-IEC, respectively. Results are shown in FIGS. 3 and 4.

Example 11

| Formulation composition | |
|---|---|
| Active Ingredient | |
| Adalimumab | 50 mg/mL |
| Inactive Ingredients | |
| Sodium succinate | 20 mM |
| Sodium chloride | 110 mM |
| Raffinose | 50 mg/mL |
| Arginine | 10 mg/mL |
| Polysorbate 80 | 0.1 mg/mL |

Adalimumab protein was prepared as per the technique known in the art and formulated in the presence of succinate buffer with arginine and raffinose as stabilizers, a suitable bulking agent and an isotonicity agent at a desired concentration as described above in the formulation composition. pH of the formulation medium was adjusted to around pH 5.2. Excipients were added to the protein solution from respective stock solutions to adjust the final concentration and volume was made up to the desired level with sterile water or Water for Injection. The formulated bulk was distributed in suitable container-closure systems (like vials, syringes etc.) for storage. Samples were exposed to the higher temperature for checking the degradation over a period of time. Samples at different time points were taken out and analyzed to estimate the aggregates and the principal charged variant of Adalimumab protein by HP-Size exclusion chromatography and HP-IEC, respectively. Results are shown in FIGS. 3 and 4.

Example 12

| Formulation composition | |
|---|---|
| Active Ingredient | |
| Adalimumab | 50 mg/mL |
| Inactive Ingredients | |
| Sodium succinate | 20 mM |
| Sodium chloride | 110 mM |
| Sorbitol | 10 mg/mL |
| Arginine | 5 mg/mL |
| Polysorbate 80 | 0.1 mg/mL |

Adalimumab protein was prepared as per the technique known in the art and formulated in the presence of succinate buffer containing arginine and sorbitol as stabilizers at a reduced concentration compared to the earlier Example 7 to reduce the osmolality. A bulking agent and an isotonicity agent were added at a desired concentration as described above. pH of the formulation medium was adjusted to around pH 5.2. Excipients were added to the protein solution from respective stock solutions to adjust the final concentration and volume was made up to the desired level with sterile water or Water for Injection. The formulated bulk was distributed in suitable container-closure systems (like vials, syringes etc.) for storage. Samples were exposed to the higher temperature for checking the degradation over a period of time. Samples at different time points were taken out and analyzed to estimate the aggregates and the principal charged variant of Adalimumab protein by HP-Size exclusion chromatography and HP-IEC, respectively. Results are shown in FIGS. 3 and 4.

Example 13

| Formulation composition | |
|---|---|
| Active Ingredient | |
| Adalimumab | 50 mg/mL |
| Inactive Ingredients | |
| Sodium succinate | 10 mM |
| Sodium chloride | 100 mM |
| Sorbitol | 10 mg/mL |
| Arginine | 5 mg/mL |
| Polysorbate 80 | 0.1 mg/mL |

Adalimumab protein was prepared as per the technique known in the art and formulated in the presence of succinate buffer with arginine and sorbitol as stabilizers, a suitable bulking agent and an isotonicity agent as described above in the formulation composition. The concentration of an isotonicity agent was reduced in comparison to the earlier Example 12 to further reduce the osmolality of the formulation medium. pH of the formulation medium is adjusted to around pH 5.2. Excipients were added to the protein solution from respective stock solutions to adjust the final concentration and volume was made up to the desired level with sterile water or Water for Injection. The formulated bulk was distributed in suitable container-closure systems (like vials, syringes etc.) for storage. Samples were exposed to the higher temperature for checking the degradation over a period of time. Samples at different time points were taken out and analyzed to estimate the aggregates and the principal charged variant of Adalimumab protein by HP-Size exclusion chromatography and HP-IEC, respectively. Results are shown in FIGS. 3 and 4.

Example 14

| Formulation composition | |
|---|---|
| Active Ingredient | |
| Adalimumab | 50 mg/mL |
| Inactive Ingredients | |
| Sodium succinate | 20 mM |
| Sodium chloride | 110 mM |
| Hydroxypropyl beta cyclodextrin | 20 mg/mL |

Figure 5:
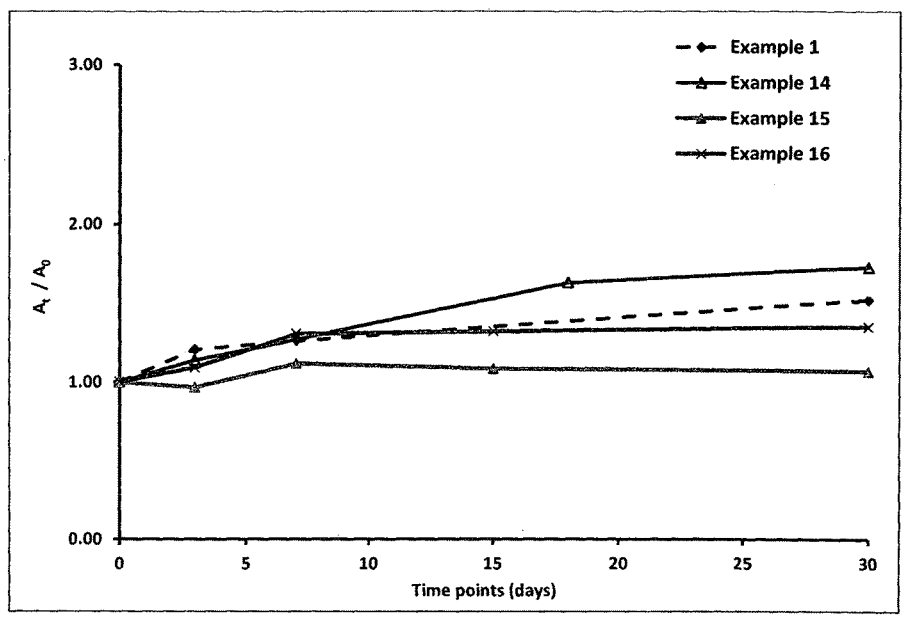
FIG. 5 shows the level of aggregates of Adalimumab protein formulated in sodium succinate buffer with different stabilizer(s), bulking agent and an isotonicity agent during storage under stressed condition. Formulation compositions are described with Examples 14 to 16.
Figure 6:
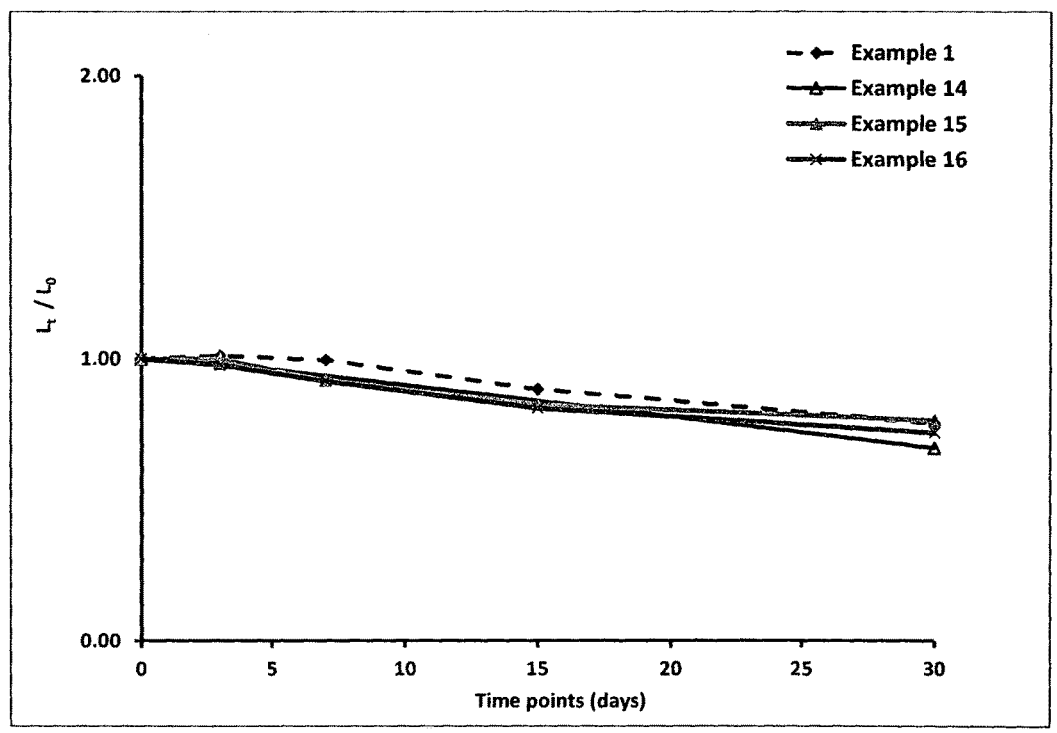
FIG. 6 shows the level of principal charged variant of Adalimumab protein formulated in sodium succinate buffer with different stabilizer(s), bulking agent and an isotonicity agent during storage under stressed condition. Formulation compositions are described with Examples 14 to 16.

Adalimumab protein was prepared as per the technique known in the art and formulated in the presence of succinate buffer further comprising hydroxypropyl beta cyclodextrin as a stabilizer along with a suitable isotonicity agent at a desired concentration as described above in the formulation composition. pH of the formulation medium was adjusted to around pH 5.2. Excipients were added to the protein solution from respective stock solutions to adjust the final concentration and volume was made up to the desired level with sterile water or Water for Injection. The formulated bulk was distributed in suitable container-closure systems (like vials, syringes etc.) for storage. Samples were exposed to the higher temperature for checking the degradation over a period of time. Samples at different time points were taken out and analyzed to estimate the aggregates and the principal charged variant of Adalimumab protein by HP-Size exclusion chromatography and HP-IEC, respectively. Results are shown in FIGS. 5 and 6.

Example 15

| Formulation composition | |
|---|---|
| Active Ingredient | |
| Adalimumab | 50 mg/mL |
| Inactive Ingredients | |
| Sodium succinate | 20 mM |
| Sodium chloride | 110 mM |
| Hydroxypropyl beta cyclodextrin | 20 mg/mL |
| Arginine | 10 mg/mL |
| Polysorbate 80 | 0.1 mg/mL |

Adalimumab protein was prepared as per the technique known in the art and formulated in the presence of succinate buffer with arginine and hydroxypropyl beta cyclodextrin as stabilizers along with a bulking agent and an isotonicity agent at a desired concentration as described above in the formulation composition. pH of the formulation medium is adjusted to around pH 5.2. Excipients were added to the protein solution from respective stock solutions to adjust the final concentration and volume was made up to the desired level with sterile water or Water for Injection. The formulated bulk was distributed in suitable container-closure systems (like vials, syringes etc.) for storage. Samples were exposed to the higher temperature for checking the degradation over a period of time. Samples at different time points were taken out and analyzed to estimate the aggregates and the principal charged variant of Adalimumab protein by HP-Size exclusion chromatography and HP-IEC, respectively. Results are shown in FIGS. 5 and 6.

Example 16

| Formulation composition | |
|---|---|
| Active Ingredient | |
| Adalimumab | 50 mg/mL |
| Inactive Ingredients | |
| Sodium succinate | 20 mM |
| Sodium chloride | 110 mM |
| Hydroxypropyl beta cyclodextrin | 20 mg/mL |
| Polysorbate 80 | 0.1 mg/mL |

Adalimumab protein was prepared as per the technique known in the art and formulated in the presence of succinate buffer containing hydroxypropyl beta cyclodextrin as a stabilizer along with a bulking agent and an isotonicity agent at a desired concentration as described above in the formulation composition. pH of the formulation medium was adjusted to around pH 5.2. Excipients were added to the protein solution from respective stock solutions to adjust the final concentration and volume was made up to the desired level with sterile water or Water for Injection. The formulated bulk was distributed in suitable container-closure systems (like vials, syringes etc.) for storage. Samples were exposed to the higher temperature for checking the degradation over a period of time. Samples at different time points were taken out and analyzed to estimate the aggregates and the principal charged variant of Adalimumab protein by HP-Size exclusion chromatography and HP-IEC, respectively. Results are shown in FIGS. 5 and 6.

The formulations described with Examples 7 to 16 are also prepared using acetate buffers or histidine buffer. Such formulations are also to be considered as being encompassed by the present invention.

The formulations of the present invention are stable when kept at 2-8° C.

The formulation of the invention can be used in similar indications as those described in U.S. Pat. Nos. 6,090,382 and 6,258,562 each of which is incorporated by reference herein. The language "effective amount" of the formulation is that amount necessary or sufficient to inhibit TNFα activity, e.g. prevent the various morphological and somatic symptoms of a detrimental TNFα activity-associated state. In one embodiment, an effective amount of the formulation is the amount sufficient to inhibit detrimental TNFα activity. The effective amount can vary depending on such factors as the size and weight of the subject, or the type of illness. One of ordinary skill in the art would be able to study the aforementioned factors and make the determination regarding the effective amount of the TNFα activity inhibiting formulation without undue experimentation.

The formulation of the present invention can be administered to the subject either prior to or after the onset of detrimental TNFα activity. Further, several divided dosages, as well as staggered dosages can be administered daily or sequentially, or the dose can be continuously infused, or can be a bolus injection. The dose can be titrated based on the exigencies of the therapeutic or prophylactic situation.

Actual dosage levels of the active ingredients (antibody) in the pharmaceutical formulation of this invention may be varied so as to obtain an amount of the active ingredient that is effective to achieve the desired therapeutic response for a particular patient, composition, and mode of administration, without being toxic to the patient. The selected dosage level will depend upon a variety of factors including the activity of the antibody found in the formulation, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known to a medical practitioner who can easily prescribe the effective amount of the pharmaceutical composition of the invention.

In general, a suitable daily dose of a formulation of the invention will be that amount of the formulation that is the lowest dose effective to produce a therapeutic effect. Such an effective dose will generally depend upon the factors described above and well known to a skilled practitioner.

It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The invention provides a pharmaceutical formulation with an extended shelf life, which, in one embodiment, is used to inhibit TNFα activity in a subject suffering from a disorder in which TNFα activity is detrimental, comprising administering to the subject an antibody or antibody portion of the invention such that TNFα activity in the subject is inhibited. Preferably, the TNFα is human TNFα and the subject is a human subject.

We claim:
1. A liquid pharmaceutical composition comprising:
  (a) an effective amount of adalimumab or an antigen binding portion thereof;
  (b) a stabilizer consisting essentially of:
    (i) from about 0.5% to about 10% arginine, or
    (ii) from about 0.5% to about 10% arginine and from about 1% to about 10% sorbitol;
  (c) 0.01% to 1% of a surfactant selected from polysorbate 80, polysorbate 20 or a combination thereof; and
  (d) 5-50 mM succinate buffer, pH 5.0 to 5.5.
2. The composition of claim 1, wherein the stabilizer consists essentially of 0.5% to about 10% arginine.
3. The composition of claim 1, wherein the stabilizer consists essentially of 5 mg/mL arginine.
4. The composition of claim 1, wherein the stabilizer consists essentially of 0.5% to about 10% arginine and from about 1% to about 10% sorbitol.
5. The composition of claim 1, wherein the stabilizer consists essentially of 5 mg/mL arginine and 10 mg/mL sorbitol.
6. The composition of claim 1, wherein the surfactant is polysorbate 80.
7. The composition of claim 6, wherein the surfactant comprises 0.1 mg/mL polysorbate 80.
8. The composition of claim 1, wherein the composition comprises 10 mM succinate buffer.
9. The composition of claim 1, further comprising a tonicity agent.

10. The composition of claim 9, wherein the tonicity agent comprises sodium chloride.

11. The composition of claim 10, wherein tonicity agent comprises from about 10 mM to about 150 mM sodium chloride.

\* \* \* \* \*